United States Patent
Chan et al.

(10) Patent No.: US 9,561,166 B2
(45) Date of Patent: Feb. 7, 2017

(54) POLYSACCHARIDE PRODUCTS WITH IMPROVED PERFORMANCE AND CLARITY IN PHOSPHATE ESTER SURFACTANT-BASED AQUEOUS FORMULATIONS AND PROCESS FOR PREPARATION

(75) Inventors: Anita N. Chan, Wilmington, DE (US); Louis Patrick Dziuk, Jr., Karnes City, TX (US); Paquita Erazo-Majewicz, Landenberg, PA (US); Jashawant J. Modi, Hockessin, DE (US); M. Olaf Michelson, Loveland, OH (US); Bruce Kevin Fillipo, Springfield, PA (US); Nabil Naouli, Wilmington, DE (US)

(73) Assignee: HERCULES INCORPORATED, Wilmington, DE (US)

( * ) Notice: Subject to any disclaimer, the term of this patent is extended or adjusted under 35 U.S.C. 154(b) by 25 days.

(21) Appl. No.: 13/400,359

(22) Filed: Feb. 20, 2012

(65) Prior Publication Data
US 2013/0216489 A1    Aug. 22, 2013

Related U.S. Application Data

(63) Continuation-in-part of application No. 13/032,263, filed on Feb. 22, 2011, now Pat. No. 8,796,196.

(60) Provisional application No. 61/308,668, filed on Feb. 26, 2010.

(51) Int. Cl.
| | | |
|---|---|---|
| *A61Q 5/02* | (2006.01) | |
| *A61K 8/92* | (2006.01) | |
| *A61K 8/55* | (2006.01) | |
| *A61Q 5/12* | (2006.01) | |
| *A61K 8/73* | (2006.01) | |

(52) U.S. Cl.
CPC .............. *A61K 8/556* (2013.01); *A61K 8/737* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | |
|---|---|---|
| 3,644,332 A | 2/1972 | Mooth et al. |
| 4,129,722 A | 12/1978 | Iovine et al. |
| 4,298,494 A | 11/1981 | Parslow et al. |
| 4,320,226 A | 3/1982 | Tiefenthaler et al. |
| 4,381,259 A | 4/1983 | Homma et al. |
| 4,645,833 A | 2/1987 | Bayerlein et al. |
| 5,489,674 A | 2/1996 | Yeh |
| 5,536,825 A | 7/1996 | Yeh et al. |
| 5,756,720 A | 5/1998 | Chawdhary |
| 6,210,689 B1 | 4/2001 | Martino et al. |
| 7,067,499 B2 * | 6/2006 | Erazo-Majewicz et al. ... 514/54 |
| 2003/0211952 A1 | 11/2003 | Erazo-Majewicz et al. |
| 2008/0263788 A1 | 10/2008 | Harrison et al. |

FOREIGN PATENT DOCUMENTS

WO        03/095497 A1     11/2003

OTHER PUBLICATIONS

Mazhar Pasha et al.: Derivatization of Guar to Sodium Carboxy Methyl Hydroxy Propyl Derivative: Characterization and Evaluation, Pak. J. Pharm. Sci., vol. 21 No. 1, Jan. 2008, pp. 40-44.
International Search Report and Written Opinion, PCT/US2011/025798, mailed Jan. 11, 2012.
Invitation to Pay Additional Fees and Partial International Search Report received in counterpart PCT Application No. PCT/US2011/025798, mailed Aug. 16, 2011 (5 pages).

\* cited by examiner

*Primary Examiner* — Tigabu Kassa
(74) *Attorney, Agent, or Firm* — Dunlap Codding P.C.; Shaorong Chen

(57) ABSTRACT

A personal or household care product includes cationic, nonionic or cationic/nonionic derivatized polysaccharide in combination with a phosphate ester surfactant. The derivatized polysaccharide polymer is formed by reacting the polysaccharide ester surfactant for a sufficient time and at a sufficient temperature in the presence of water, caustic, and at least one surfactant. The polysaccharide polymer may optionally be reacted with an oxidizing agent, hydrolytic or proteolytic enzymes, molecular weight reducing agents and a cationizing agent and nonionic agent. The formed derivatized polysaccharide has a lower clarity in water than in an aqueous surfactant system.

16 Claims, No Drawings

POLYSACCHARIDE PRODUCTS WITH IMPROVED PERFORMANCE AND CLARITY IN PHOSPHATE ESTER SURFACTANT-BASED AQUEOUS FORMULATIONS AND PROCESS FOR PREPARATION

RELATED APPLICATIONS

This application is a continuation-in-part application which is related to and claims the benefit of U.S. patent application Ser. No. 13/032,263, filed Feb. 22, 2011, which, in turn, claims the benefit of U.S. Provisional Patent Application Ser. No. 61/308,668, filed Feb. 26, 2010, the disclosures of which are incorporated herein by reference.

FIELD OF THE INVENTION

The present invention relates to polysaccharide compositions and more particularly cationic anionic, nonionic or amphoteric polysaccharide compositions which, when added to various personal care or household care compositions, yields a relatively transparent composition.

BACKGROUND OF THE INVENTION

Personal care compositions containing cationic polymers have been found to deliver rheology, thickening, lather richness and conditioning benefits to hair and skin substrates. Cationic polymers also improve deposition of other active benefiting agents such as silicone and silicone derivatives, anti-dandruff agents, color, moisturizing agents, emollients. The cationic polymers can be based on polysaccharide backbones or on synthetic polymer backbones or mixture thereof.

Cationic polysaccharides and other polymers have been used widely in personal care, household, industrial, and institutional products to perform various benefiting agent functions in the final product, ranging from the use of the polymer as gellants, binders, thickeners, stabilizers, emulsifiers, spreading, lathering and deposition aids. Cationic polysaccharides and other polymers also function as carriers for enhancing the conditioning, anti-microbial activities, lubrication, rheology, efficacy, deposition, moisturizing, color, lather, emolliency, aesthetics as well as for the delivery of chemically and physiologically active ingredients in personal care, household, institutional and industrial compositions. Depending on the application, substrates to which the personal care, household, industrial, and institutional product is applied can be skin, hair, or textile substrates.

Cationic polymers have been used in hair care products to provide conditioning, moisturizing, anti-static, deposition of color, other conditioning and non-conditioning agents, deposition of fragrance to the hair. In addition, in hair care products they provide for deposition of anti dandruff/anti-microbial agent to hair and scalp. In skin care products, these same polymers can provide conditioning effects to the skin. In addition, they provide moisturizing, lubrication, deposition of color, other conditioning and non-conditioning agents, deposition of fragrance, and deposition of anti dandruff/antimicrobial agent. When incorporated into detergent and/or fabric softening formulations, these same polymers can provide conditioning, softening, anti-abrasion and anti-static characteristics to fabrics.

Wet and dry combability and friction measurements are typical test methods used to measure conditioning performance of polymers in shampoo and conditioner applications. Friction values are also frequently used to reflect conditioning benefits to skin. Commercial cationic conditioning polymers in shampoo formulations have been reported to reduce the wet combing force experienced on combing wet hair by 5%-99% relative to the shampoo containing no polymer. The performance of different cationic polymers in these applications varies. However, typically it is desirable that shampoos contain cationic polymers to achieve a good balance of wet and dry combing force reduction, with good optical clarity in a formulation.

For example, cationic galactomannan polymers, such as cationic guar, and other polymers originating from seeds or other natural origins, contain insoluble components which can include protein components, which may interact with surfactants in the formulation, leading to unstable and opaque formulations. Since the conditioning performance of the polymer is strongly related to its solubility in and interactions with the surfactants in the formulation, it is desirable to improve the solubility of the conditioning polymer in the surfactant system which in effect improves the clarity of the surfactant-based formulation.

EP1501873 A1 addresses the need for a cationic galactomannan polymer with good optical clarity in personal care, household, and fabric cleansing formulations.

U.S. Pat. No. 6,210,689 discloses an amphoteric guar composition for treating keratin substances.

U.S. Pat. No. 5,756,720 describes a process for producing a polygalactomannan composition having nonionic and cationic groups attached to the backbone to achieve high optical clarity in cleansing surfactant formulations.

WO99/36054 describes hydroxypropyl modified cationic polygalactomannans, which have been found lacking in conditioning performance.

U.S. Pat. No. 4,381,259 describes shampoo compositions containing cationic polymers and improvements in shampoo performance by addition of phosphoric acid ester surfactants to the shampoo composition. This patent does not discuss shampoo compositions with combined improved deposition of benefit agents and enhanced clarity in the formulation.

U.S. Pat. No. 4,298,494 describes shampoo compositions containing cationic polygalactomannan gums and anionic additives to improve deposition onto hair from the shampoo. This patent does not discuss surfactant compositions with improved clarity in the formulation.

U.S. Pat. No. 5,489,674 describes a process for preparing polygalactomannan gums using an aqueous alcohol slurry process, the resulting product giving 85-100% transmittance at wavelengths between 500-600 nm at 0.5 parts polymer in 100 parts of an aqueous solution. The use of this material in personal care applications is disclosed.

U.S. Pat. No. 5,536,825 discusses a process for producing a derivatized guar gum composition that demonstrates greater than 75% light transmission at a wavelength from about 500-600 nanometers when dispersed in water in the amount of about 0.5 parts per 100 parts water and use of this composition in personal care compositions.

U.S. Pat. No. 7,067,499 discloses a composition comprising at least one cationic polygalactomannan having a lower limit mean average MW of 5,000 and an upper limit MW of 200,000, having a light transmittance in aqueous solution at 10 wt % polymer concentration of at least 80% at a wavelength of 600 nm, and a protein content less than 1% based on polysaccharide content, and an aldehyde content of at least 0.01 meq/g, where optical clarity is achieved through the use of a filtration process or other processes.

Cationic polysaccharides based on cellulosic backbones, such as UCare Polymer JR400 having a high cationic substitution, are known to give good clarity in a broad range of surfactant systems. However, these polymers have also been cited by the manufacturer as giving "buildup" problems on the hair after repeated use.

U.S. Pat. No. 4,129,722 describes the use of surfactants in polysaccharide processing for producing water-soluble or water-swellable polysaccharide derivatives having a high degree of substitution (DS), from 0.05-2.5 DS, comprising suspending the polysaccharide in an organic solvent, immiscible with the aqueous derivatizing reagent phase, in the presence of cationic, anionic, or nonionic surfactants. This patent does not discuss processing in aqueous processes or improved clarity of the resulting products in surfactant-based systems.

Consequently, there still exists a need in the marketplace for personal care and household care formulations with enhanced conditioning performance, including silky feel to the substrate, such as hair, skin, or textile fabric, enhanced deposition of active materials and conditioning agents, and improved clarity and improved aesthetics, such as shampoo clarity, and essentially no buildup of polymer or conditioning components after repeated use without the need for removal of insoluble material from the polysaccharide or the use of solvents to clarify the product. Also, the need exists for a process to produce these polysaccharides in an aqueous-based process rather than a solvent containing process.

SUMMARY OF THE INVENTION

Applicants specifically incorporate by reference the entire contents of all cited documents in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It has been found unexpectedly that cationic, anionic, nonionic or amphoteric polysaccharide polymers such as cationic galactomannan polymer compositions having high clarity in surfactant-based compositions can be produced by inclusion of materials such as surfactants during the preparation of the polymer compositions using an aqueous-based process. The present invention relates to a process for preparing a cationic, nonionic, amphoteric, or anionic polysaccharide polymer composition having high clarity in surfactant-based compositions and to the product produced through this process.

The process of the present invention comprises the steps of: reacting a polysaccharide polymer or derivatized polysaccharide polymer for a sufficient time and at a sufficient temperature in the presence of water, caustic and at least one surfactant. The reaction can be conducted with other processing steps. The process may additionally comprise reacting the polysaccharide polymer or derivatized polysaccharide polymer for a sufficient time and at a sufficient temperature with an oxidizing agent such as hydrogen peroxide or other reactant such as hydrolytic or proteolytic enzymes, acids, or other agents that reduce the molecular weight of the polysaccharide or galactomannan polymer or associated protein or other polysaccharide components.

The process may also comprise reacting the polysaccharide polymer or derivatized polysaccharide polymer for a sufficient time and at a sufficient temperature with a compound containing either hydrocarbon functionality, such as alkyl or hydroxyalkyl compounds, anionic functionality, such as a carboxylic acid compound, a sulfonic acid compound, a phosphoric acid compound, a phosphate compound, or cationic functionality, such as a primary, secondary, or tertiary amino compound or quaternary ammonium compound containing groups capable of reacting with reactive hydrogen ions present on the polysaccharide or derivatized polysaccharide to produce the nonionic, anionic, or cationic polysaccharide polymer composition. The polysaccharide polymer composition may also contain combinations of these groups.

The present process comprises using a surfactant, such as nonionic surfactants, such as polysorbate surfactants such as Tween 20 or Tween 60, or anionic surfactants such as fatty acids, phosphate ester surfactants, alkyl sulfate or alkyl ether sulfate surfactants, cationic surfactants such as tertiary amine or quaternary ammonium surfactants or mixtures during the production steps for the polysaccharide. An individual surfactant can be used alone or in combination with other surfactants, including other nonionic surfactants, carboxylate surfactants, sulfate or sulfonic acid surfactants, phosphate or phosphonic acid surfactants, amine or quaternary ammonium surfactants during the production steps for polysaccharide derivatives.

The present invention is directed to a composition of at least one polysaccharide, especially polysaccharides derived from natural sources, such as polygalactomannan or derivatized galactomannan polymers having a weight average molecular weight (Mw) in the range of from about 5,000 to about 10,000,000 and having a water-soluble and water-insoluble fraction, wherein the water-insoluble fraction constitutes greater than 0.4 wt % % of the composition and the polymer having an aqueous clarity at 1 wt % of less than 60% light transmittance at a wavelength between 500-600 nm and clarity greater than 85-90% light transmittance at a wavelength of between 500-600 nm, in a surfactant system, when the nonionic, anionic, amphoteric or cationic polysaccharide polymer is present at a concentration of up to 0.2% by weight of the composition.

This invention is further directed to a process for preparing the composition mentioned above including the steps of reacting at least one polysaccharide, especially a galactomannan polymer or derivatized galactomannan polymer in the presence of at least one surfactant and an oxidizing agent, biochemical agents such as hydrolytic or proteolytic enzymes, acids, bases, or other agents that reduce the molecular weight of the polysaccharide or galactomannan polymer, associated protein, or other polysaccharide components, to produce the polysaccharide composition of the invention, or derivatized polysaccharide of the invention containing anionic, nonionic, or cationic, or amphoteric moieties, or combinations thereof.

This invention is further directed to a composition of a functional system of personal care products, household care products, and pet care products containing the above mentioned polysaccharide, or derivatized polysaccharide, especially a cationic or nonionic polygalactomannan or derivatized cationic or nonionic polygalactomannan composition. A second component of the composition is a phosphate ester surfactant or surfactant blend which includes a phosphate ester. An optional component is a compatible solvent which may also be used in the functional composition that can be either a single solvent or a blend of solvents, and optionally at least one active personal care, household care, or pet care ingredient, respectively.

This invention is further directed to a composition of a functional system of personal care products, household care products, and pet care products, especially surfactant compositions that contain the above mentioned polysaccharide, derivatized polysaccharide, galactomannan polymer, or derivatized galactomannan polymer, a phosphate ester surfactant or surfactant mixture which includes a phosphate ester, and optionally a synthetic polymer that increases deposition of the derivatized polysaccharide or polygalactomannan polymer and any disperse phase components in the composition.

The use of the polymer compositions of the invention is also contemplated in other formulated products where surfactant compositions are used such as oilfield, mining, coating, pharmaceutical, and constructions, fire retardant, under water explosive applications.

DETAILED DESCRIPTION OF THE INVENTION

The process of the present invention comprises reacting a polysaccharide polymer with water, caustic and a surfactant. The reacted polysaccharides exhibit improved light transmittance in an aqueous surfactant solution when compared to the light transmittance of the polymer in an aqueous solution without the surfactant. The invention also includes the method of making the modified polysaccharide. The present invention provides a polysaccharide or derivatized polysaccharide polymer which includes anionic, cationic, nonionic or amphoteric moiety (or combinations thereof). Further, the present invention may be used to provide a polysaccharide polymer having a reduced molecular weight with improved light transmittance in an aqueous surfactant solution.

It has been found unexpectedly that polysaccharides such as galactomannan polymer compositions having anionic, nonionic, cationic, or amphoteric moieties (or mixtures thereof) with improved clarity in surfactant-based compositions can be produced by inclusion of anionic, nonionic, amphoteric, betaine, or cationic surfactants such as 1) a combination of reagents such as polyoxyethylene sorbitol alkyl or alkenyl ester surfactants, or 2) alkylpolyethyleneoxide carboxylate surfactants, or 3) fatty acid surfactants and mixtures of fatty acids, in the processing of the polysaccharide or galactomannan polymer compositions. This list of surfactants is illustrative in nature, and not intended to be exhaustive.

In accordance with this invention, an oxidative reagent can be used in combination with the surfactant in addition to other reagents, including biochemical reagents, that reduce molecular weight. In order to achieve optimum results, it is preferable to include the surfactant and the oxidative step in the process. Oxidative agents include any reagent that can act to reduce the molecular weight of the polymer. Examples of these oxidizing agents are peroxides, peracids, persulfates, permanganates, perchlorates, hypochlorate, and oxygen. Optionally, biochemical reagents that reduce molecular weight, or acids or bases that reduce molecular weight of polysaccharides or associated protein components, may also be present.

In accordance with the invention, the polymers that can be used in the invention include polysaccharides, derivatized or nonderivatized, especially polygalactomannan, polyglucomannan, agar, dextran, starch, polyglucomannan polymers, xanthan polymers, and other polysaccharides.

The preferred polygalactomannans of this invention are guar, locust bean, cassia, fenugreek, locust, and flame tree with guar gum being the preferred source of the polygalactomannan. The preferred polygalactomannan starting material used in this invention is guar flour, guar powder, guar flakes, guar gum, or guar splits, including purified and highly purified sources of the galactomannan polymer. The preferred polysaccharide backbone is polygalactomannan, such as guar, locust bean gum, cassia gum, tara gum, and other polysaccharides, such as galactomannan or glucomannan polymers, e.g., konjac gum or aloe gum.

In one embodiment, the polysaccharide polymer is reacted with functional groups such as anionic, cationic, or nonionic functional groups in the presence of caustic and the surfactant.

The amount of anionic, nonionic, or cationic functional group bonded to on the polysaccharide can be expressed in terms of moles of substituent. The term "degree of substitution" as used in this invention is equivalent to the molar substitution, the average number of moles of functional groups per anhydro sugar unit in the polysaccharide. The functionality can be present on these polymers at a DS level as low as 0.01, preferably about 0.1, and more preferably 0.2. The DS upper limit is normally about 3.0, preferably about 2.0, and more preferably 1.0 and most preferably below 0.7. In addition to molar substitution, the anionic or cationic charge on the polymers of this invention can be quantified as a charge density. The molar substitution can be converted to a charge density through a variety of methods. The preferred method for calculating charge density of cationic polymers uses a method that specifically quantifies the equivalents of quaternary ammonium groups on the polymer. A starting material having a cationic molar substitution level of 0.18 has been determined to have a charge density of 0.95 equivalents per gram (meq/g) according to the following equation:

Cationic charge density of DS 0.18 cationic polysaccharide=$(1000\times0.18)/(162.14+(151.64\times0.18))$= 0.95 meq/g.

Charge density can be measured by any method that quantifies the net positive or negative charge present on a polymer. The charge density can be determined by measurement of the moles of quaternary ammonium groups bound to the polymer backbone using standard NMR techniques of integration. This method was used for determining the charge density for polymers of this invention.

The cationic, anionic, nonionic or amphoteric functionality of the polysaccharide or derivatized polysaccharide can be added by several methods. For example, the starting polysaccharide material is contacted with caustic and water to swell the polymer, and the swollen mass can be reacted for a sufficient time and at a sufficient temperature, typically at between 40-70 degrees Celsius for 1-2 hours, with, for example, tertiary amino compound or quaternary ammonium compound containing groups capable of reacting with the reactive hydrogen ions present on the polysaccharide or derivatized polysaccharide in order to add the cationic functionality to the starting material. The reaction is conducted in the presence of a surfactant where the surfactant is present at a concentration ratio to the polysaccharide of 0.005-0.9, more preferably 0.01-0.5, and most preferably 0.01-0.1. Crosslinking reagents, e.g., sodium borate, zirconates, titanates, or others known in the art, are then added and the product is washed, dried and ground. The sufficient time depends on the ingredients in the reaction mass and the temperature under which the reaction is taking place and the desired viscosity of the final product in aqueous solution.

The cationizing agent of the present invention is defined as a compound which, by substitution reaction with the hydroxy groups of the polygalactomannan, can make the polygalactomannan electrically positive, and there is no limitation to its types. Primary, secondary, or tertiary amino compounds or various quaternary ammonium compounds containing groups capable of reacting with reactive hydrogen present on the polygalactomannan, can be used, such as 2-dialkylaminoethyl chloride and quaternary ammonium compounds such as 3-chloro-2-hydroxypropyltrimethylammonium chloride, and 2,3-epoxy-propyltrimethylammonium chloride. Preferred examples include glycidyltrialkylammonium salts and 3-halo-2-hydroxypropyltrialkylammonium salts such as glycidyltrimethylammonium chloride, glycidyltriethylammonium chloride, gylcidyltripropylammonium chloride, glycidylethyldimethylammonium chloride, glycidyldiethylmethylammonium chloride, and their corresponding bromides and iodides; 3-chloro-2-hydroxypropyltrimethylammonium chloride, 3-chloro-2-hydroxypropyltriethylammonium chloride, 3-chloro-2-hydroxypropyltripropylammonium chloride, 3-chloro-2-hydroxypropylethyldimethylammonium chloride, and their corresponding bromides and iodides; and quaternary ammonium compounds such as halides of imidazoline ring containing compounds.

The polysaccharides may also be reacted in the presence of surfactants with other substituent groups such as (1) nonionic substituents, i.e., hydroxyalkyl wherein the alkyl represents a straight or branched hydrocarbon moiety having 1 to 30 carbon atoms (e.g., hydroxyethyl, hydroxypropyl, hydroxybutyl) or, (2) anionic substituents, such as carboxymethyl groups, sulfonate groups, or phosphate or phosphonate groups. The nonionic substituents are linked to the polysaccharide polymer by the reaction with reagents such as (1) alkylene oxides (e.g., ethylene oxide, propylene oxide, butylene oxide) to obtain hydroxyethyl groups, hydroxypropyl groups, or hydroxybutyl groups, and the anionic substituents are linked to the polysaccharide by reaction with reagents such as (2) chloromethyl acetic acid to obtain a carboxymethyl group, or with sulfonyl chloride to obtain sulfonic acid groups on the polysaccharide, or with phosphonyl chloride or other anion containing groups capable of reacting with the reactive hydrogen ions present on the polysaccharide or derivatized polysaccharide in order to add the anionic functionality to the starting material. The sufficient time depends on the ingredients in the reaction mass and the temperature under which the reaction is taking place. The process for preparing derivatized polygalactomannan is well known in the art.

The anionic or cationic polysaccharide of the invention can also contain alkyl or acyl substituents wherein the alkyl or acyl group represents a straight or branched alkyl group or alkylcarboxylic or alkylenecarboxylic moiety, respectively, having 1 to 30 carbon atoms. These optional substituents can be reacted with the polysaccharide molecule in the presence of surfactant by the reaction of the polysaccharide molecule with reagents such as (1) alkyl halides to obtain alkyl functionality, (2) acyl chlorides, anhydrides, esters, or ketenedimer reagents to obtain ester or amide functionality, (3) alkylene oxides (e.g., ethylene oxide, propylene oxide, butylene oxide) to obtain hydroxyethyl groups, hydroxypropyl groups, or hydroxybutyl groups. If the polysaccharide is polygalactomannan, this derivatization reaction can take place when the polygalactomannan is in the "split", "flour", or any other physical form. The process for preparing derivatized polygalactomannan is well known in the art. These optional substituents can be introduced into the polysaccharide structure.

If the polysaccharide is polygalactomannan, this reaction can take place when the polygalactomannan is in the "split", "flour" or any other physical form. The process for preparing derivatized polygalactomannan is well known in the art.

In accordance with this invention, the formed derivatized polysaccharide or polygalactomannan composition of the invention contains a water-soluble and water-insoluble fraction, where-in the water-insoluble fraction comprises up to 3 wt % of the polymer composition, more preferable up to about 1-3 wt % of the composition, and generally up to 0.4-2 wt % of the composition of the invention. The water-insoluble fraction contains greater than 10 wt % protein component, more preferably greater than 12 wt % protein, and most preferably greater than 16 wt % protein.

In accordance with this invention, the formed polysaccharide or polygalactomannan composition of the invention has a percent light transmittance in water at 1 wt % polymer concentration of less than 60% at a wavelength of about 500-600 nm.

In accordance with this invention, the polysaccharide or polygalactomannan composition of the invention has a percent light transmittance in a surfactant system composed of 12% sodium lauryl ether sulfate surfactant/2% cocamidopropyl betaine surfactant, of greater than 85% transmittance, generally greater than 90% transmittance, at a wavelength of between 500-600 nm when the polymer is present at a concentration of 0.2 wt %. The cationic polysaccharide, especially the cationic polygalactomannan of the invention, will have a percent light transmittance in a surfactant system consisting of 12 wt % sodium laureth sulfate/2 wt % cocamidopropyl betaine/1 wt % sodium chloride, greater than 85% transmittance, more preferably greater than 90%-95% transmittance at a wavelength of about 500-600 nm, when the polymer is present at a concentration of 0.2% by weight of the composition.

The polysaccharide polymer such as the guar can also be reacted under the same conditions without any functional group, only the caustic, water, oxidizing agent, and surfactant. This will provide a polymer with the same light transmittance qualities.

Further, the polysaccharide polymer may be reacted under these same conditions, time, and temperature, with caustic, surfactant and an oxidative reagent. In order to achieve optimum results, it is necessary to include the surfactant and the oxidative step in the process. Oxidative agents include any reagent that can act to reduce the molecular weight of the polymer. Examples of these oxidizing agents are peroxides, peracids, persulfates, permanganates, perchlorates, hypochlorite, and oxygen.

The derivatized polysaccharide of the invention, especially polysaccharides such as galactomannan polymers, will have a weight average molecular weight (Mw) having a lower limit of 5,000, preferably 25,000, more preferably 100,000, and most preferably 200,000. The upper limit of the Mw of these polymers is less than 10,000,000, preferably 5,000,000, and more preferably 2,000,000.

In accordance with this invention, the polysaccharide or polygalactomannan composition of the invention has a percent light transmittance in a surfactant system, of greater than 85% transmittance, generally greater than 90% to 95% transmittance, at a wavelength of between 500-600 nm. The modified polysaccharide that was modified with a cationic moiety will have a percent light transmittance in a surfactant system consisting of 12 wt % sodium laureth sulfate/2 wt % cocamidopropyl betaine/1 wt % sodium chloride, greater than 85% transmittance, more preferably greater than 90-95% at a wavelength of between 500-600 nm, when the polymer is present at a concentration of 0.2% by weight of the composition.

In accordance with this invention, if the product of the invention is a cationic polysaccharide, the cationic polygalactomannan or cationic derivatized polygalactomannan composition has a trimethylamine content in a 0.5% aqueous solution of less than 100 ppm, preferably less than 75 ppm, and most preferably less than 25 ppm when measured by any method known to those skilled in the art. Examples of methods used to measure trimethylamine include gas chromatography (GC), mass spectrometry, solid phase extraction methods using fiber adsorbents, and combinations thereof.

The polysaccharide of the present invention can be combined with a nonionic, anionic, cationic, or amphoteric surfactant or mixture of these surfactants, or a phosphate ester surfactant or surfactant mixture which includes a phosphate ester, that can be either soluble or insoluble in the composition, and optionally combined with a compatible solvent which may also be used in the cleansing composition that can be either a single solvent or a blend of solvents to produce a personal care composition, household care composition, or other composition. Personal care compositions include hair care, skincare, sun care, and oral care products. Household care compositions include dishwashing detergents, laundry detergents and fabric softeners, industrial grade soap bars and liquid soaps, textile products such as wipes, insect repellants.

The polysaccharide of use in the present invention is one component of the composition. A second component of the composition is a phosphate ester surfactant or surfactant mixture which includes a phosphate ester. If the surfactant is a phosphate ester, the polysaccharide should be a cationically or nonionically modified polysaccharide. An optional component is a compatible solvent which may also be used in the cleansing composition that can be either a single solvent or a blend of solvents.

Examples of the surfactants useful in these compositions are anionic, nonionic, zwitterionic, cationic, or amphoteric type of surfactants, and blends thereof. The anionic, nonionic, zwitterionic, cationic, or amphoteric surfactant can be soluble or insoluble in the present invention and (when used) are present in the composition in the amount of from 0.01 to about 75 wt % by weight of the cleansing composition.

Anionic surfactants useful in the functional system composition include alkyl and alkyl ether sulfates, alkyl sulfosuccinates, and fatty acids and phosphate ester surfactants as nonlimiting examples and generally any anionic surfactants typically used in cleansing, conditioning, and detergent compositions.

The phosphate esters for use in the present invention can be a mixture of mono-, di-ester, or coester phosphates of alkoxylated and non-alkoxylated alcohols containing between 6 and 32 carbon atoms. Preferred alcohols contains between 16 and 22 carbon atoms. Most preferably an alcohol known as oleyl alcohol is employed, which contains an average C18 hydrophobic chain. The phosphate esters of the alkoxylated and non-alkoxylated fatty alcohols of the present invention are formed by reacting alkoxylated and non-alkoxylated fatty alcohols, respectively, with phosphorus pentoxide (P2O5) or polyphosphoric acid, or a combination. The alkoxylated alcohols preferably have between about 1 and 20 moles of the alkoxylating moieties present for each alcohol moiety where the alkoxylated moiety is preferably either derived from ethylene oxide or propylene oxide, or combination.

In general, phosphate esters of the present invention can be mixtures of mono-, and di-esters or coesters of alkoxylated alkyl, alkoxylated alkenyl, alkoxylated aryl, alkoxylated aryl alkyl/alkenyl and/or alkyl, alkenyl, aryl or alkyl aryl/alkenyl phosphate esters with a structure summarized below:

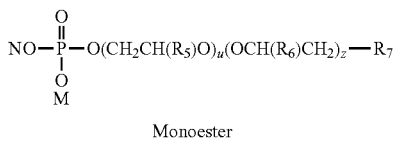

Monoester

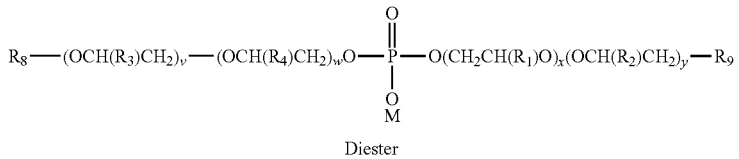

Diester

Where:
  M and N are hydrogen atoms, an alkali metal atom, an alkaline earth, amine, alkanol amine or ammonium
  R1, R2, R3, R4, R5, R6 are hydrogen, methyl, ethyl, propyl or butyl groups
  $R_7$, $R_8$ and $R_9$ are alkyl, alkenyl, alkyl aryl or alkenyl aryl groups, fluorinated alkyl, alkenyl, alkyl aryl or alkenyl aryl groups, or organosilicone, or combinations (co-ester) thereof
  u, v, w, x, y and z range from 0-20

In the case of oleyl phosphate or oleth-5-phosphate, the phosphate ester is a mono-, di-ester mixture at a stoichiometric ratio typically at ~1.5 mono/diester and:
  u, v, x, z, w, y are a value between 0 and 5
  R2, R4, R6=hydrogen atom
  R7, R8 and R9=oleyl Preferred anionic surfactants are phosphate ester surfactants at a concentration of from about 1 to about 6% phosphate ester surfactant mixture (mono- and di-ester), with the diester components comprising up to 75% of the mixture by weight of the composition. Other anionic surfactants include sodium or ammonium $C_{12}$-$C_{14}$ alkyl sulfates, and sodium or ammonium $C_{12}$-$C_{14}$ alkyl ether sulfates having 1 to 3 moles ethylene oxide. An anionic surfactant system can comprise from about 4 to about 15% sodium lauryl sulfate and from about 3 to about 10% sodium lauryl ether sulfate.

Nonionic surfactants, can be broadly defined as compounds containing a hydrophobic moiety and a nonionic hydrophilic moiety. Examples of the hydrophobic moiety can be alkyl, alkyl aromatic, dialkyl siloxane, polyoxyalkylene, and fluoro-substituted alkyls. Examples of hydrophilic moieties are polyoxyalkylenes, phosphine oxides, sulfoxides, amine oxides, and amides. Nonionic surfactants such as alkylpolyglucosides and other nonionic surfactants commonly used in cleansing, conditioning, and sulfate free formulations are also useful in this invention.

Zwitterionic surfactants are exemplified by those which can be broadly described as derivative of aliphatic quaternary ammonium, phosphonium, and sulfonium compounds.

Examples of amphoteric surfactants which can be used in the personal care composition of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

According to the present invention, the solvent used in the personal care or household care system should be compatible with the other components of the cleansing composition. Examples of the solvents that may be used in the present invention are water, water-lower alkanols mixtures, and polyhydric alcohols having from 3 to 6 carbon atoms and from 2 to 6 hydroxyl groups. Preferred solvents are water, polyethylene glycol, propylene glycol, water-polyethylene glycol, water-propylene glycols, water-glycerine, sorbitol-water, water-fragrance and water-ethanol. The solvent (when used) in the present invention is present in the composition at a level of from 0.1% to 99% by weight of the composition.

In certain instances, an active ingredient or benefiting agent is optional because the polymer combined with phosphate ester can be the active ingredient component. An example of this is the use of the polymer in an aqueous solution as a conditioner for hair or skin conditioning, as a fabric conditioner, or as an antimicrobial agent.

In accordance with the present invention, the composition may be used in a personal care product, a household care product or an institutional care product. The composition is a personal care product when it contains at least one active personal care ingredient or benefiting agent, the personal care active ingredient or benefiting agent includes, but is not limited to, analgesics, anesthetics, antibiotic agents, antifungal agents, antiseptic agents, antidandruff agents, antibacterial agents, vitamins, hormones, anti-diarrhea agents, corticosteroids, anti-inflammatory agents, vasodilators, kerolytic agents, dry-eye compositions, wound-healing agents, anti-infection agents, UV absorbers, moisturizers, humectants, emolliency, lubricating, softening, hair-detangling, hair relaxers, hair sculpturing, hair removing, dead-skin removing, as well as solvents, diluents, adjuvants and other ingredients such as water, ethyl alcohol, isopropyl alcohol, propylene glycol, higher alcohols, glycerine, sorbitol, mineral oil, preservatives, surfactants, propellants, fragrances, essential oils, and viscosifying agents.

Personal care compositions include hair care, skin care, sun care, nail care, and oral care compositions. Examples of active personal care ingredients or benefiting agents that may suitably be included, but not limited to, in the personal care products according to the present invention are as follows:

1) Perfumes, which give rise to an olfactory response in the form of a fragrance and deodorant perfumes which in addition to providing a fragrance response can also reduce body malodor;
2) Skin coolants, such as menthol, menthyl acetate, menthyl pyrrolidone carboxylate N-ethyl-p-menthane-3-carboxamide and other derivatives of menthol, which give rise to a tactile response in the form of a cooling sensation on the skin;
3) Emollients, such as isopropylmyristate, silicone materials, mineral oils and vegetable oils which give rise to a tactile response in the form of an increase in skin lubricity;
4) Deodorants other than perfumes, whose function is to reduce the level of or eliminate micro flora at the skin surface, especially those responsible for the development of body malodor. Precursors of deodorants other than perfume can also be used;
5) Antiperspirant actives, whose function is to reduce or eliminate the appearance of perspiration at the skin surface;
6) Moisturizing agents, that keep the skin moist by either adding moisture or preventing from evaporating from the skin;
7) Sunscreen active ingredients that protect the skin and hair from UV and other harmful light rays from the sun. In accordance with this invention a therapeutically effective amount will normally be from 0.01 to 10% by weight, preferable 0.1 to 5% by weight of the composition;
8) Hair treatment agents, that condition the hair, cleanse the hair, detangles hair, acts as styling agent, volumizing and gloss agents, color retention agent, anti-dandruff agent, hair growth promoters, hair dyes and pigments, hair perfumes, hair relaxer, hair bleaching agent, hair moisturizer, hair oil treatment agent, and antifrizzing agent; and
9) Oral care agents, such as dentifrices and mouth washes, that clean, whiten, deodorize and protect the teeth and gum.

In accordance with the present invention, the composition may be used in a household care composition. The household care composition additionally comprises and at least one active household care ingredient or benefit agent. The household care active ingredient or benefit agent must provide some benefit to the user. Examples of active ingredients that may suitably be included, but not limited to, according to the present invention are as follows:

1) Perfumes, which give rise to an olfactory response in the form of a fragrance and deodorant perfumes which in addition to providing a fragrance response can also reduce odor;
2) Insect repellent agent whose function is to keep insects from a particular area or attacking skin;
3) Bubble generating agent, such as surfactant that generates foam or lather;
4) Pet deodorizer or insecticides such as pyrethrins that reduces pet odor;
5) Pet shampoo agents and actives, whose function is to remove dirt, foreign material and germs from the skin and hair surfaces;
6) Industrial grade bar, shower gel, and liquid soap actives that remove germs, dirt, grease and oil from skin, sanitizes skin, and conditions the skin;

7) Disinfecting ingredients that kill or prevent growth of germs in a house or public facility;
8) A laundry softener active, which reduces static and makes fabric feel softer;
9) Laundry or detergent or fabric softener ingredients that reduce color loss during the wash, rinse, and drying cycle of fabric care;
10) Toilet bowl cleaning agents, which remove stains, kills germs, and deodorizes;
11) Laundry prespotter actives which helps in removing stains from clothes;
12) Fabric sizing agent which enhances appearance of the fabric; and
13) Wipes to clean and condition the skin The above lists of personal care and household care active ingredients or benefit agents are only examples and are not complete lists of active ingredients that can be used. Other ingredients that are used in these types of products are well known in the industry. In addition to the above ingredients conventionally used, the composition according to the present invention can optionally also include ingredients such as a colorant, preservative, antioxidant, nutritional supplements, alpha or beta hydroxy acid, activity enhancer, emulsifiers, functional polymers, viscosifying agents (such as salts, i.e., NaCl, $NH_4Cl$, and KCl, water-soluble polymers, i.e., hydroxyethylcellulose and hydroxypropylmethylcellulose, and fatty alcohols, i.e., cetyl alcohol), alcohols having 1-6 carbons, fats or fatty compounds, antimicrobial compound, zinc pyrithione, silicone material, hydrocarbon polymer, emollients, oils, surfactants, medicaments, flavors, fragrances, suspending agents, and mixtures thereof.

In accordance with the present invention, examples of functional polymers that can be used in blends with the anionically, nonionic, amphoteric, or cationically modified polysaccharide of this invention include water-soluble polymers such as acrylic acid homopolymers such as carbomers, vinylpyrrolidone homopolymers and cationic vinylpyrrolidone copolymers; cationic acrylamide copolymers such as acrylamide copolymers with cationic monomers such as acrylamidopropyl trimethyl ammonium chloride, acryloxyethyl trimethyl ammonium chloride, or diallyldimethyl ammonium chloride, and anionic and amphoteric acrylic acid copolymers, hydrophobically modified carbomers, vinylpyrrolidone homopolymers and cationic vinylpyrrolidone copolymers; nonionic, cationic, anionic, and amphoteric cellulosic polymers such as hydroxyethylcellulose, hydroxypropylcellulose, carboxymethylcellulose, hydroxypropylmethylcellulose, cationic hydroxyethylcellulose, cationic carboxymethylhydroxyethylcellulose, and cationic hydroxypropylcellulose; acrylamide homopolymers and anionic, cationic, amphoteric, and hydrophobic acrylamide copolymers, polyethylene glycol polymers and copolymers, hydrophobic polyethers, hydrophobic polyetheracetals, hydrophobically-modified polyetherurethanes and other polymers referred to as associative polymers, hydrophobic cellulosic polymers, polyethyleneoxide-propylene oxide copolymers, and nonionic, anionic, hydrophobic, amphoteric, and cationic polysaccharides such as xanthan, chitosan, starch, carboxymethyl guar, alginates, gum arabic, nonionic, cationic, anionic, and amphoteric guar polymers such as hydroxypropyl guar, hydrophobic guar polymers, carboxymethyl guar hydroxypropyltrimethylammonium chloride, guar hydroxypropyltrimethylammonium chloride, and hydroxypropyl guar hydroxypropyltrimethylammonium chloride.

In accordance with the invention, the silicone materials which can be used are polyorganosiloxanes that can be in the form of polymers, oligomers, oils, waxes, resins, or gums or polyorganosiloxane polyether copolyols, amodimethicones, cationic polydimethylsiloxane materials and any other silicone material that is used in personal care compositions, household care compositions or institutional care compositions.

The polysaccharides of use in this invention can be used as conditioning agents in shampoos, 2-in-1 shampoos, 3-in 1 shampoo (cleansing, conditioning and styling), conditioners, hair colors and relaxers, body washes, shave products, bar soaps, body lotions, sunscreens, antifrizz and hair styling formulations. The polysaccharides of use in this invention can also be used to improve hair volume, manageability, hair repair, or color retention, skin moisturization and moisture retention, fragrance retention, sunscreen longevity on hair, skin, and fabrics, flavor enhancement and antimicrobial performance in oral care applications, and improve fabric abrasion resistance and colorfastness in household applications.

The polymers of this invention possess an ability to deliver formulations having improved clarity across a range of surfactant systems and across a range of polymer concentrations, in personal care and household products.

It has also been demonstrated that the polymers of this invention can deliver conditioning effects in addition to high clarity in personal care products and in other surfactant-based products, such as household products.

It has also been demonstrated that the polymers of this invention enhance deposition of conditioning oils onto keratin substrates, such as skin and hair, improving the conditioned state of the substrate.

It has also been demonstrated that the polymers of this invention enhance deposition of any dispersed phase ingredients onto the treated substrate, the dispersed phase ingredients including benefit agents such as antidandruff, fragrance, sunscreen or sun protection factors (SPFs).

The invention is further demonstrated by the following examples. The examples are presented to illustrate the invention, parts and percentages being by weight, unless otherwise indicated.

Standard Testing Methods & Procedures

Aqueous Polymer Solution Preparation and Measurement of Percent Transmittance and Viscosity One gram of polymer was added to 99 grams deionized water and stirred with a mechanical stirrer at 600 rpm. For galactomannan polymer compositions that were treated with borate salts, 10 wt % citric acid solution was added to the dispersion to reduce the pH of the solution to 5.5 to effect dissolution of the polymer in water. The mixture was stirred at ambient temperature for an additional 50 minutes and the final solution was left to stand overnight at ambient temperature. The solution was then analyzed for optical clarity by measuring the % transmittance of light of 600 nm wavelength through the sample on a Cary 5E spectrometer. A separate sample of the solution was placed in a suitable glass container and maintained at 25 C for 2 hours prior to measuring the viscosity on a Brookfield LVT Model with the appropriate spindle at 30 rpm.

Surfactant Solution Transmittance

The optical clarity of the aqueous polymer solutions and shampoo formulations were measured on a Cary spectrometer, at a wavelength of 600 nm. This specific percent transmittance data is shown since the percentage transmittance of light through a sample at a wavelength of 600 nm has been correlated with the optical clarity of a solution. In the absence of any absorbance at 600 nm, an optically clear solution is considered to have a percent transmittance greater than 95%.

Optical Clarity of Aqueous Polymer Solutions and Shampoo Formulations

Optical Clarity. The percent transmittance data at 600 nm for selected samples in water, in the shampoo formulations 1-4 and in shampoo formulation 5, are shown in Tables 4 and 5, respectively. This specific percentage transmittance data is shown since the percentage transmittance of light through a sample at a wavelength of 600 nm has been correlated with the optical clarity of a solution. In the absence of any absorbance at 600 nm, an optically clear solution is considered to have a percent transmittance @ 600 nm greater than 95%, preferably greater than 97% and more preferably greater than 99%.

The percent transmittance was measured at a wavelength of 600 nm for (1) a 1 wt % aqueous solution of the polymers of the invention and comparative polymers, and (2) in the surfactant compositions in Table 1 (also referred to as Shampoo Formulations 1-4) and Table 2 (referred to as shampoo formulation 5). Shampoo formulations 2 contains 0.2 wt % of each polymer in a surfactant composition containing: 12 wt % sodium laureth sulfate (2 ethylene oxide spacers)/2 wt % cocamidopropyl betaine/1 wt % sodium chloride. This specific percentage transmittance data was chosen because the percentage transmittance of light through a sample at a wavelength of 600 nm has been correlated with the optical clarity of a solution visible to the eye. In the absence of any absorbance at 600 nm, an optically clear solution is considered to have a percent transmittance @ 600 nm greater than 90%, preferably greater than 92%, and more preferably greater than 95%.

Insoluble Content of Polymer

Isolation of Insolubles from Cationic Guar.

A 0.5%-0.8% solution of cationic guar was prepared in deionized water and stirred for 1 to 2 hours. The pH was adjusted to approximately 5 with hydrochloric acid. The solution was stirred for an additional 1 to 2 hours, allowed to stand in a refrigerator for at least 16 hours, and stirred again.

The solution was centrifuged in portions and the nearly clear supernatant layer was removed. The precipitates were dispersed in water and combined. The solutions were centrifuged again and the supernatant was removed. The dispersion and centrifugation was repeated as least three times. The total dilution of the precipitate by repeated dispersion was at least 1000 times by volume. All solutions and precipitates were kept refrigerated when not being processed.

The final precipitate and a portion of the original supernatant solution were freeze dried for further analysis. The concentration of insolubles in the cationic guar was calculated by dividing the weight of the freeze dried precipitate by the original weight of sample.

Soluble Content of Polymer

The water-soluble content of the polymer was then calculated by subtracting the insoluble weight of the polymer measured as described above, from the original polymer weight.

Wt % Nitrogen and Total % Protein

The nitrogen content of the polysaccharide compositions was determined using elemental analysis using inductively coupled plasma technique. The resulting data correlated well with Kjeldahl measurements of nitrogen content and estimates of nitrogen content using NMR measurements of the cationic substitution level. The protein content was then calculated by multiplying the % Nitrogen by 6.25 per standard methods for conversion of nitrogen content to protein content. (Food Energy: Methods of Analysis and Conversion Factors, Chapter 2: Methods of Food Analysis; Food and Agricultural Organization of the United Nations.)

Galactose/Mannose Ratio Measurements

The anomeric protons of galactose and mannose units were identified in the proton NMR spectrum of the acid hydrolysates of the various polymers, and the galactose/mannose ratio was determined by standard methods. (P. 4592-4593 in J. O. Duus et al, Chem. Rev. 2000, 100, 4589-4614.)

Molecular Weight Determinations

Size exclusion chromatography was used for molecular weight analysis. Weight average molecular weights were determined using a light scattering detector. Separations were effected using an oxalic acid mobile phase at pH 2 on a column.

Cationic Substitution and Hydroxypropyl Substitution Measurements

The degree of cationic and hydroxypropyl substitution was measured using proton NMR according to standard methods, on an acid hydrolysate of the polymer sample.

Shampoo Preparation A: Shampoo Formulations 1, 2, 3, 4

The conditioning shampoo formulations referred to in Table 4 were prepared by combining 73 parts by weight (pbw) of the following surfactant premix composition shown in Table 1 with 6.7 pbw deionized water and 13.3 pbw of the polysaccharides or modified polysaccharides of use in the invention, as a 1.5 wt % aqueous solution, using a Caframo overhead mechanical stirrer with a dispersion blade, stirring at 600 rpm. After allowing the composition to mix for 45 minutes at ambient temperature, the formulation was allowed to remain at ambient temperature overnight. The viscosity and pH value of the formulation was recorded, with pH values ranging from 5.5-6.0.

Four pbw of a sodium chloride salt solution (25 wt %) and 3 pbw of water was then added to the shampoo, and stirring commenced for an additional 15 minutes. The shampoo compositions were maintained at ambient temperature overnight, and the viscosity of each shampoo was measured using a Brookfield LVT viscometer with a Brookfield LVT viscometer, spindle 4, at 30 rpm.

TABLE 1

Premix and Shampoo Formulation Compositions

| Ingredient | INCI Name | wt % Active in Shampoo 1 Formulation | wt % Active in Shampoo 2 Formulation | Shampoo 1 & 2 premix | wt % Active in Shampoo 3 Formulation | Shampoo 3 premix | wt % Active in Shampoo 4 Formulation | Shampoo 4 premix |
|---|---|---|---|---|---|---|---|---|
| Deionized water | Deionized water | qs to 100 | qs to 100 | 2308.00 | qs to 100 | 1089.33 | qs to 100 | 1409.33 |
| Standapol ® | Sodium laureth | 12.00 | 12.00 | 5760.00 | 10.00 | 1600.00 | 8.00 | 1280.00 |

TABLE 1-continued

Premix and Shampoo Formulation Compositions

| Ingredient | INCI Name | wt % Active in Shampoo 1 Formulation | wt % Active in Shampoo 2 Formulation | Shampoo 1 & 2 premix | wt % Active in Shampoo 3 Formulation | Shampoo 3 premix | wt % Active in Shampoo 4 Formulation | Shampoo 4 premix |
|---|---|---|---|---|---|---|---|---|
| ES-2 | sulfate-2EO (25%) | | | | | | | |
| Amphosol ® CA | Cocamidopropyl Betaine (30%) | 2.00 | 2.00 | 800.00 | 2.00 | 266.67 | 2.00 | 266.67 |
| Kathon ® CG | Biocide | 0.10 | 0.10 | 12.00 | 0.10 | 4.00 | 0.10 | 4.00 |
| | | | | 8880.00 | | 2960.00 | | 2960.00 |
| | polymer | 0.5% | 0.2 wt % | | 0.2 wt % | | 0.2 wt % | |

1. Standapol ES-2 sodium laureth sulfate (2EO) Cognis
2. Amphosol CA cocamidopropyl betaine, Stepan Chemical Co.
3. Kathon CG preservative: Dow Chemical Co.

Shampoo Preparation B, Shampoo 5

A series of sulfate free shampoos were prepared with the premix in Table 2 to produce Shampoo formulation 5 in Table 2.

TABLE 2

Shampoo 5 Premix and Composition

| Ingredient | INCI Name | wt % As-is in Shampoo 5 Formulation | Parts in premix |
|---|---|---|---|
| Deionized water | Deionized water | qs to 100 | 1592.00 |
| Amphosol ® CA (Stepan Chemical) | Cocamidopropyl betaine (30%) | 15.00 | 600.00 |
| Maprosyl ®30B (Stepan Chemical) | Sodium lauroylsarcosinate (30%) | 10.00 | 400.00 |
| Mackam ®1L (Cognis) | Sodium lauroamphoacetate (35%) | 6.00 | 240.00 |
| Glycerin | Glycerin, anhydrous | 1.00 | 40.00 |
| Plantaren ® 2000 N UP (Cognis) | Alkylpolyglucosides | 2.00 | 80.00 |
| Disodium EDTA | Disodium EDTA | 0.10 | 4.00 |
| Kathon ® CG (Dow Chemical) | Biocide | 0.10 | 4.00 |
| | | | 2960.00 |
| | Polymer | 0.50 | |

Shampoo Preparation, Shampoo 6

A series of shampoos were prepared with the silicone microemulsion (Dow Corning® 1784 emulsion, available from Dow Corning Corporation) using the premix for formulation 2 in Table 1, with 0.4 pbw Carbomer 980 (Carbopol 980, available from Lubrizol Corporation), and 1.5 wt % active silicone (Dow Corning® 1784 emulsion, available from Dow corning corporation) and 0.2 wt % polymer. These shampoo formulations and data are shown in Tables 5 and 6.

Silicone deposition from Shampoo formulation 6 was measured as described below, as a model for assessing deposition effectiveness of the polymers of the invention for deposition of benefit agents from personal care formulations, household formulations, and industrial formulations. Silicone deposition was measured by treating virgin brown hair with the shampoo formulation 6 containing the polymers of the invention and polymers in comparative examples. The silicone deposition data is shown in Table 5.

Conditioning Performance Measurements-Deposition Measurements

In order for a conditioning shampoo to perform on hair, deposition of a material must occur, to reduce interfiber friction in the wet and dry states, reduce comb energies in the wet and dry state.

Wet and dry hair combability measurements are typical test methods used to measure conditioning performance in shampoo and conditioner applications. In skin care applications, skin lubricity or reduced friction or softer feel of the skin, reduced water vapor transmission and improved skin elasticity are test methods used to measure skin conditioning. In surfactant-based household cleansing product formulations where conditioning performance is desired, such as dish detergents, fabric softeners, and antistatic products, conditioning refers to imparting a softer feel to fabric and eliminating static effects, eliminating fabric fiber breakage or deformation known as pilling. Imparting color retention properties to fabrics is also important and can be measured.

Wet/Dry Comb Performance Measurement—Virgin Brown European Hair and Lightly Bleached Medium Brown Hair Conditions:

Measured at constant temperature and humidity (72° F. and 50% relative humidity).

Prewash Procedure:

Each tress washed twice with sodium lauryl sulfate, SLS, or other anionic surfactants, e.g., sodium lauryl ether sulfate (SLES) using 0.1 g-5 g surfactant/gram tress, washing twice then air drying overnight at 73° F. and 50% relative humidity. The twice washed tress was hand combed 5 times with large teeth comb and 5 times with small teeth comb (10 times total).

The following protocol was used for bleached and virgin hair. Two to three tresses were used, and the average reported from the two to three tresses combed 8 times per tress, with more precombing of the tresses prior to measurement as described above.

Shampoo Procedure

1. Each tress was shampooed twice with 0.1 g shampoo per 1 gram tress (all tresses were 3.0 g).
2. Each shampooed tress was hand combed twice with a large teeth comb.
3. The hand combed tress was loaded into a Instron instrument and the crosshead was lowered to bottom stop. The tress was combed twice with small teeth comb and placed into double-combs.

The Instron was run under standard conditions.
After the test was run, the tress was sprayed with DI water to keep moist.
4. After the eight tests were finished, the tress was hung up overnight.
5. The next day, each tress was dry combed tested eight time. No hand combing of dry tresses was done.
6. Averaged wet comb energy for 16 Instron runs and reported average with standard deviation.
7. Averaged dry comb energy for 15 Instron runs and reported average with standard deviation.

Silicone deposition onto hair tresses from shampoos and zinc deposition onto artificial skin can be measured by several techniques. One nondestructive technique used for quantifying silicone deposition onto hair and one technique quantifying zinc deposition onto solid substrates such as artificial skin are described below.

Zinc and Silicone Deposition Measurements on Vitro-Skin Substrate.

The vitro-skin was cut into 2.5 cm disks, and the disks were analyzed under vacuum via x-ray fluorescence spectroscopy on a Bruker model S4 Explorer X-ray Fluorescence (SRF) Spectrometer for zinc (Zn). The approximate detection limit for each element is 50 parts per million (0.0050 wt %). This method had been previously verified with direct measurement of inorganic ions in the ashed model skin substrate using inductively coupled plasma (ICP).

Silicone Deposition Measurement

For total silicone deposited on hair tresses, each 2-5 gram hair tress sample was weighed to the nearest mg and extracted with approximately 150 ml of methylene chloride. The samples were shaken for 1.5 hours at room temperature. The methylene chloride supernatant was filtered using Whatman #41 filter paper and evaporated to dryness. Each sample was then dissolved into 2 ml of chloroform-d and quantitatively transferred to a 5-ml volumetric flask. Each sample was examined in a NICOLET MAGNA 550 FT-IR with 150 co-added scans at 4 cm-1 resolution and 0.4747 velocity using a 0.1 cm-fixed path salt cell. A chloroform-d reference spectrum was used to subtract out the solvent bands (diff=1.0). The silicone level was determined by measuring the peak height of the Si—CH3 stretch at 1260 cm-1 (baseline 1286 and 1227 cm-1) followed by conversion to mg/ml of silicone using a low level calibration curve extending from 10-300 parts per million (ppm). Each sample was corrected for dilution volume and sample weight. All values are reported to the nearest ppm.

Silicone Mapping Along Tress Length

The relative concentration of the silicone deposit along the length of a hair tress was mapped using a surface infrared technique, attenuated total reflectance-infrared spectroscopy (ATR-IR). The ATR-IR technique uses the ratio of the peak height of the silicone band near 796.5 $cm^{-1}$ (tangent baseline), to an area slice of a hair reference band from 940.1 $cm^{-1}$ to 919.9 $cm^{-1}$ (tangent baseline) to determine the relative surface silicone level according to equation 1. This method of surface silicone measurement was shown to have a correlation with total extracted silicone levels across a range of 300 ppm to 4000 ppm.

Ratio: Peak Height at 796.5 $cm^{-1}$/Peak Area (940.1 $cm^{-1}$ to 919.9 $cm^{-1}$=Relative Surface Silicone Level (detection limit=0.05)  (eq 1)

The technique may be used to measure approximately 10-20 strands of hair in one measurement with a 1 mm circular spot. A bundle of fibers from each tress is positioned on a Golden Gate* diamond ATR accessory of the Thermo-Nicolet MAGNA* 760 FTIR spectrometer equipped with a deuterated triglycine sulfate (DTGS) detector. Infrared spectra are collected at 12 different locations on the hair tress starting from the top and working towards the bottom of the tress.

Static Measurement of Treated Hair Tress

Static charge measurements were conducted on 3 gram hair tresses using a Faraday cage. The tress was placed in a constant temperature/humidity room overnight at 50% relative humidity and 73 degrees Fahrenheit before running the test. Tresses had been combed 3 times with a large tooth comb and 3 times with a small tooth comb prior to the measurement. A static gun was passed over the tress, back and front, 1 time, while outside of the Farady cage, prior to the static measurement. The tress was placed into the Faraday cage and a rotating brush contacted the tress for 20 revolutions, and the static measurement was taken at this time.

Coefficient of Friction

Coefficient of Friction Measurements on Dry Hair—Friction measurements were obtained on a CETR UMT* M0 tribometer using a sledge friction test with a silicon wafer counter surface at 23° C. and 50% relative humidity on dry hair samples under a constant load of 300 mN and a sliding speed of 0.5 mm/s.

EXAMPLES

Comparative Example 1

An amount of guar splits, water and caustic solution as shown in Table 3 were charged to the mixer. The temperature was raised to between 40-60° C. The 3-chloro-2-hydroxypropyltrimethylammonium chloride (quat reagent), additional caustic solution, water, and sodium borate decahydrate were then added, and the reaction was allowed to proceed for 1 hour. After cooling to ambient temperature, the crude product was washed with water, and dried and ground.

Example 2

Example 2 was prepared by the same process as Example 1, except that the surfactants polyoxyethylene sorbitan monoleate and polyoxyethylene sorbitan monolaurate, were added in the first step.

Comparative Example 3

The prescribed amount of guar splits, water and hydrogen peroxide solution as shown in Table 3 were charged to the mixer. The mixture was processed at a temperature between 40-60° C. for up to 3 hours. The 3-chloro-2-hydroxypropyltrimethylammonium chloride (quat reagent), additional caustic and water, and sodium borate decahydrate were then added, and the mixture was processed at a temperature between 40-60° C. for up to 2 hours. After cooling to ambient temperature, the crude product was washed with water, and dried and ground.

Comparative Example 4

100 parts of guar splits and 152 parts of 18% caustic solution were charged to the mixer. The temperature was raised to 65° C. and held there for 1 hour. After cooling to ambient temperature, the splits were washed with water followed by 30%, 60% and 80% isopropanol. The splits were then returned to the mixer. The temperature was raised to 41° C., and vacuum was applied to remove the isopropanol. The process for Example 3 was then followed to convert the guar gum into cat guar.

Examples 5, 6, 9, 10, 15

Examples 5, 6, 9, 10 and 15 were prepared by the same process as Example 3, except that the polysorbate surfactants Tween 20 and Tween 80 were added in the first step. These examples demonstrate a cationic polygalactomannan product of the invention produced by the process of the invention.

Example 5a was prepared by the same process as Example 5 with its ingredients shown in Table 3, except that propylene oxide was reacted with the guar splits at 70° C. for up to 3 hours prior to addition of the quat reagent. This example demonstrates a mixed derivative, cationic hydroxypropyl guar product of the invention, prepared by the process of the invention.

Comparative Examples 7-8

Comparative Example 7 was prepared by the same process as in Example 3 with its ingredients shown in Table 3. Comparative Example 8 came from Comparative Example 7 where a portion of the product received additional washing.

Examples 11-14

Examples 11, 12, and 14 were prepared by the same process as Comparative Example 8, except that various surfactants as indicated in Table 3 were added. Higher purity splits were used in Examples 7, 8, 11, 12, and 14.

Example 13 came from Example 12 where a portion of the product was washed with water containing 2% of a sodium laureth-13-carboxylate anionic surfactant (Sandopan® LS 24N surfactant available from Clariant Corp).

Examples 16-22

Examples 16-22 represent comparative Examples of commercial cationic guar polymers.

Examples 23-27

Examples 23, 24 and 26 were replicates of Example 5 produced at a larger scale.
Example 25 is a replicate of comparative Example 3 produced at a larger scale.
Example 27 is a replicate of comparative Example 11 produced at a larger scale.

Examples 28-35

Example 28 is a clear shampoo formulation of the invention containing the polymer of the invention of Example 24.
Example 29 is a clear shampoo formulation of the invention containing the combination of the polymer of the invention of Example 24 with a phosphate ester surfactant.
Example 30 is a silicone shampoo formulation of the invention containing the polymer of the invention of Example 24.
Examples 31 and 32 are comparative examples containing the shampoo surfactant and the shampoo surfactant with phosphate ester, respectively.
Examples 33, 34, and 35 are comparative examples of shampoos containing the cationic guar of Example 19 that does not yield clear formulations, with examples 33 and 35 also containing phosphate ester surfactant.

TABLE 3

Example Reaction Compositions

| | Comp Ex 1 | Ex 2 | Comp 3 | Comp 4 | Ex 5 | Ex 5a | Ex 6 | Comp Ex 7 | Ex 9 | Ex 10 | Ex 11 | Ex 12 | Ex 14 | Ex 15 |
|---|---|---|---|---|---|---|---|---|---|---|---|---|---|---|
| Guar splits (99%) | 100 | 100 | | | | | | 100 | | | 100 | 100 | 100 | |
| Guar splits (93%) | | | 100 | 100 | 100 | 100 | 100 | | 100 | 100 | | | | 100 |
| Water | 59 | 59 | 51 | 40 | 59 | 82 | 58 | 56 | 60 | 64 | 62 | 62 | 62 | 40 |
| Surfactant | 0 | 5 (1) | | | 5 (1) | 5 (1) | 0.85 (2) | 0 | 5 (1) | 5 (1) | 5 (1) | 5 (3) | 0.8 (4) | 5 (1) |
| 30% Hydrogen peroxide | | | 3 | 2 | 2 | 1 | 2 | 3 | | 1 | 2 | 2 | 2 | 1 |
| 50% Sodium hydroxide | 21 | 21 | 22 | 23 | 21 | 22 | 20 | 20 | 23 | 24 | 21 | 21 | 21 | 40 |
| Propylene oxide | | | | | | 20 | | | | | | | | |
| 65% 3-Chloro-2-Hydroxypropyltrimetylammonium chloride (Quat 188) | 36 | 36 | 46 | 48 | 40 | 54 | 34 | 33 | 53 | 54 | 36 | 36 | 36 | 40 |
| Sodium borate decahydrate (Borax) | 1 | 1 | 1 | 1 | 1 | 1 | 1 | 1 | 1 | 1 | 1 | 1 | 1 | 1 |
| 80% Acetic Acid | | | | | | | | | | | 4 | | | 4 |

(1) 3 parts Polyoxyethylene (20) sorbitan monolaurate (Tween ® 20)/2 parts Polyoxyethylene (20) sorbitan monooleate (Tween ® 80)
(2) 0.51 parts Polyoxyethylene (20) sorbitan monolaurate (Tween ® 20)/0.3 parts Polyoxyethylene (20) sorbitan monooleate (Tween ® 80)
(3) Sodium laureth-13-carboxylate anionic surfactant (Sandopan ® LS 24N surfactant available from Clariant Corp) (69%)
(4) Mixture 0.4 parts lauric acid/0.4 parts oleic acid The improved clarity of the products of the invention when used at a concentration of 0.5 wt % (Shampoo 1) and 0.2 wt % (Shampoo 2) is demonstrated in Table 4. The polymer of the invention in Examples 2, 5, 6, 9, 10, 11, 13 and 15 produced shampoo formulations with the highest clarity, relative to the comparative control polymers. This conclusion is drawn by comparing the % transmittance of Shampoo 2 in Table 4 for the following: a) Shampoo 2 containing polymers of the invention in Example 2 has higher % transmittance when compared with Comparative Example 1, b) Shampoo 2 containing polymers of the invention in Examples 5, 6, 9, 10, and 15 have higher % transmittance when compared with comparative example 3, and c) Shampoo 2 containing polymers of the invention in Examples 11, 12, 13, and 14 have higher % transmittance when compared with Comparative Example 8.

It is instructive to discuss the % transmittance of these polymers in aqueous solution at a concentration of 1 wt % polymer and in surfactant composition Shampoo 2 at a concentration of 0.2 wt % polymer.

As shown by the aqueous solution clarity of the 1% polymer solution in comparative Example 4, it is shown that caustic extraction of the guar as defined in U.S. Pat. No. 5,489,674 does improve aqueous solution clarity of the polymer, as well as reducing protein content of the polymer. However, increasing aqueous polymer solution clarity by caustic extraction did not deliver improved clarity of the Comparative Example 4 in shampoo formulation 1, as shown by its low % transmittance in shampoo 1 when the polymer is present at a concentration of 0.5 wt %.

By using the % transmittance as a measure of clarity of shampoo 1 in Table 4, it is apparent that the higher optical transmittance for Example 2 relative to comparative Example 1 and for Example 5 relative to Comparative Example 3 demonstrate the improved clarity in surfactant-based systems such as shampoo formulation 1, provided by the polymer of the invention in Examples 2 and 5. Comparison of the optical clarity of shampoo 1 formulation containing Example 6 relative to Example 5 demonstrates that the concentration of surfactant in the process affects the clarity of the resulting polymer in the surfactant system of shampoo 1 and other surfactant systems. Comparison of the optical clarity of shampoo 1 formulation containing comparative Example 8 with Comparative Example 7 demonstrates that extra washing at the end of the process does not improve the clarity of the standard processed polymer in surfactant-based systems.

In shampoo formulation 2 in Table 4, the polymers of the invention in Examples 5, 9, 10, 11, 13, and 15 have higher clarity than either of the comparative control polymers in Examples 3, or 8. Similarly, in shampoo formulation 2, the polymers of the invention in Examples 5, 9, 10, 11, 13, and 15 have higher clarity than the Comparative controls in Examples 16, 18, 19, and 22.

The % transmittance values for the shampoo formulations 2, 3, and 4 in Table 4 demonstrate the impact of decreasing surfactant concentration on optical clarity of the shampoo. Shampoo formulations 2-4 containing the polymer of the invention in Example 11 consistently have higher % transmittance values, correlated with optical clarity, than the corresponding shampoos containing the polymer in comparative Example 8 or any of the comparative Examples 16, 18, 19, or 22.

Polymers of the invention in Examples 2, 5, 6, 9, 10, 11, 12, 13, and 14 demonstrate the impact of a variety of surfactant charge types and structures in the process for producing the product of the invention, as well as their use in a post washing procedure (Example 13).

Polymer of the invention in Example 5a demonstrates a cationic hydroxypropyl guar of the invention.

The % transmittance of 1% aqueous solutions of the polymers of the invention in Examples 2, 5, 5a, 6, 9, 10, 11, 12, 14, and 15 is less than 60% when measured at 600 nm wavelength, similar to the % transmittance for the polymers in comparative Examples 1, 3, and 8, 16, 18, 19, 20, and 22. Unexpectedly, the polymers of the invention in Examples 2, 5, 5a, 9, 10, 11, 13, 15, 23, and 24 have aqueous solution transmittance of less than 55% when the polymer is present at a concentration of 1 wt %, but % transmittance values of 85% or higher in shampoo formulation 2 in Table 4, which consists of 12% sodium lauryl ether sulfate, 2% cocamidopropyl betaine surfactants and 1 wt % sodium chloride. In addition, the polymer of the invention in Examples 11, 15, 23, and 24 deliver shampoos having % transmittance values of 85-90% in shampoo formulations 2-4 in Table 4 and in the sulfate-surfactant-free shampoo formulation 5 in Table 5, when the polymer is present at 0.2 wt % and 0.5 wt % in the formulations, respectively. The comparative Example 8 shows only 83-85% transmittance in shampoo formulations 2-4 in Table 4 and less than 75% transmittance in shampoo formulation 5 in Table 5 when the polymer is present at 0.2 wt % and 0.5 wt % in the formulations, respectively. The polymers in comparative Examples 16-22 show less than 80% transmittance in shampoo formulations 2-4 and less than 80% transmittance in shampoo formulation 5 when the polymer is present at 0.2 wt % and 0.5 wt % in the formulations, respectively. The polymer of comparative Example 20 is one exception, in that the polymer of comparative Example 20 had >80% transmittance when the polymer is present in solution at a concentration of 1 wt %, making this polymer different from the polymers of the invention, which have <60% transmittance in aqueous solution when the polymer is present at a concentration of 1 wt %.

The polymer of comparative Example 21 shows properties similar to the polymers of the invention in Examples 11, 23, 24, 26 and 27 in terms of its low % transmittance in aqueous solution, and >85% transmittance in the shampoo formulations 2-4 in Table 4 and shampoo 5 in Table 5. However, the polymers of the invention in Examples 26 and 27 have an insoluble content >0.4 wt %, greater than the insoluble content of the polymer of comparative example 21. In addition, the polymers of the invention demonstrate better performance as deposition agents for dispersed phase components, or benefit agents, such as silicone or zinc, onto substrates such as hair. For example, in Table 5, the polymers of the invention in Example 11, 23, and 24 in shampoo formulation 6 lead to 40-80%-improvement in silicone deposited onto the hair substrate relative to the shampoo formulation 6 containing the comparative polymer in example 8 and greater than 40%-80% improvement in silicone deposition onto hair when compared with the polymer in comparative Example 21.

As shown in Table 6, the clarity of the formulation of the invention in Example 29, which contains both the cationic guar of the invention and a phosphate ester surfactant, is >95% transmittance at 600 nm, outperforming the clarity of cationic guar formulations in comparative Examples 33, 34, and 35. In addition, Example 29 in Table 6 delivers better conditioning performance, as demonstrated by lower wet and dry comb energies, lower dry friction, and lower static to both brown and bleached hair, when compared with the comparative examples 31, 32, and 34. The conditioning performance of this formulation is better than the conditioning performance of the cationic guar of the invention in the absence of phosphate ester surfactant in Example 28. The formulation of the invention in Example 29 also outperforms the conditioning performance and has better clarity than the comparative formulation of example 30, which is a silicone shampoo formulation containing the cationic guar of the invention without phosphate ester surfactant.

In summary, the polymers of the invention are improvements over the polymers in the comparative Examples.

In addition, the protein content for the polymers of the invention in Examples 2, 5, 6, 9, 10, 11, 12, 14, and 15 is similar to the protein content of their comparative examples 1, 3, and 8. Yet the clarity of shampoo formulation 2 containing the polymers of the invention in Examples 2, 5, 6, 9, 10, 11, 12, 14, and 15 is greater than the clarity of the shampoos containing the respective comparative control polymers in Examples 1, 3, and 8.

The low shampoo clarity of the shampoo containing the polymer of Comparative Example 4 demonstrates that the process of U.S. Pat. No. 5,756,720 reduces protein content and improves aqueous solution clarity of the polymer but not surfactant-based formulation clarity.

TABLE 4

Polymer Compositions and Shampoo Performance-Shampoos 1-4

| example | Cationic Substitution | Hydroxypropyl Substitution | Gal/Man ratio | Molecular weight | % T@ 600 nm aq polymer @1% | Visc/cps @ 1 wt % | % protein | % Nitrogen Total | % T@ 600 nm Shampoo 1 - [polymer] = 0.5 wt % |
|---|---|---|---|---|---|---|---|---|---|
| 1 | 0.196 | | 0.643 | | 24 | 75400 | 1.31 | 1.59 | 31 |
| 2 | 0.189 | | 0.665 | | 20 | 69200 | 1.31 | 1.54 | 42 |
| 3 | 0.203 | | 0.587 | 329,000 | 41 | 38 | 1.19 | 1.67 | 61 |
| 4 | 0.239 | | 0.586 | 404,000 | 75 | 67 | 0.06 | 1.77 | 48 |
| 5 | 0.198 | | 0.557 | 441,000 | 39 | 72 | 1.38 | 1.63 | 69 |
| 5a | 0.267 | 0.54 | 0.71 | | 19 | 458 | 1.96 | 2.18 | |
| 6 | 0.174 | | 0.565 | 397,000 | 33 | 58 | 1.44 | 1.5 | |
| 7 | 0.162 | | 0.615 | 301,000 | 35 | 26 | 1.31 | 1.34 | 55 |
| 8 | | | | | 37 | 25 | | | |
| 9 | 0.233 | | 0.592 | | 41 | 50 | 1.13 | 1.87 | |
| 10 | 0.25 | | 0.568 | 953,000 | 45 | 1025 | 1.25 | 1.96 | |
| 11 | 0.171 | | 0.643 | 325,000 | 39 | 34 | 1.31 | 1.42 | 68 |
| 12 | 0.172 | | 0.652 | 287,000 | 41 | 26 | 1.38 | 1.49 | 72 |
| 13 | | | | | 43 | 24 | | | 70 |
| 14 | 0.173 | | 0.653 | 306,000 | 32 | 23 | 1.44 | 1.52 | 61 |
| 15 | 0.196 | | 0.566 | 580,000 | 51 | 360 | 1.38 | 1.64 | |
| 16 (1) | 0.147 | | 0.587 | 300,000 | 22 | 59 | 1.19 | 1.16 | |
| 17 (1) | 0.171 | | 0.574 | | 41 | 29 | 1.00 | 1.36 | 35 |
| 18 (1) | 0.158 | | 0.605 | 1,140,000 | 46 | 4060 | 1.06 | 1.23 | |
| 19 (1) | 0.225 | | 0.576 | 1,070,000 | 40 | 3700 | 1.00 | 1.81 | |
| 20 (2) | 0.231 | | 0.632 | 837,000 | 56 | 960 | 0.25 | 1.7 | |
| 21 (2) | 0.168 | | 0.645 | 311,000 | 40 | 48 | 0.75 | 1.29 | |
| 22 (2) | 0.14 | | 0.624 | 1,030,000 | 35 | 5260 | 1.06 | 1.1 | |
| 23 | 0.182 | | 0.593 | 313,000 | 22 | 54 | 0.75 | 1.41 | |
| 24 | 0.175 | | 0.591 | 320,000 | 43 | 39 | 0.69 | 1.36 | |
| 25 | 0.172 | | 0.566 | 334,000 | 52 | 34 | 0.81 | 1.35 | 42 |
| 26 | 0.171 | | 0.567 | 334,000 | 52 | 40 | 1.00 | 1.38 | |
| 27 | 0.168 | | 0.651 | 255,000 | 55 | 18 | 0.69 | 1.33 | |

| example | Shampoo 1 Visc/cps | % T@ 600 nm Shampoo 2 - [polymer] = 0.2 wt % | Shampoo 2 Visc/cps | % T@ 600 nm Shampoo 3 - [polymer] = 0.2 wt % | Shampoo 3 Visc/cps | % T@ 600 nm Shampoo 4 - [polymer] = 0.2 wt % | Shampoo 4 Visc/cps | Polymer Wt % Insolubles |
|---|---|---|---|---|---|---|---|---|
| 1 | 12340 | 62 | 6379 | | | | | |
| 2 | 11320 | 72 | 6319 | | | | | |
| 3 | 6260 | 86 | 4159 | | | | | |
| 4 | 12700 | | | | | | | |
| 5 | 6080 | 89 | 4599 | | | | | |
| 5a | | 97 | 3323 | | | | | |
| 6 | 9120 | | | | | | | |
| 7 | 4780 | | | | | | | |
| 8 | | 83 | 7280 | 83 | 1448 | 85 | 333 | |
| 9 | | 90 | 3539 | | | | | |
| 10 | | 88 | 4849 | | | | | |
| 11 | 4960 | 93 | 7360 | 89 | 1376 | 87 | 335 | |
| 12 | 8420 | | | | | | | |
| 13 | 8400 | 91 | 3159 | | | | | |
| 14 | 7000 | | | | | | | |
| 15 | | 88 | 7620 | 86 | 1960 | 83 | 652 | |
| 16 (1) | | 68 | 5600 | 72 | 1768 | 82 | 430 | |
| 17 (1) | 10378 | | | | | | | |
| 18 (1) | | 47 | 9280 | 50 | 2768 | 50 | 1016 | |
| 19 (1) | | 77 | 10200 | 72 | 2792 | 69 | 1116 | |
| 20 (2) | | 97 | 8760 | 99 | 2352 | 97 | 844 | |

TABLE 4-continued

Polymer Compositions and Shampoo Performance-Shampoos 1-4

| | | | | | | | | |
|---|---|---|---|---|---|---|---|---|
| 21 (2) | | 95 | 6080 | 95 | 1700 | 92 | 426 | 0.3 |
| 22 (2) | | 53 | 11600 | 58 | 3620 | 56 | 1280 | |
| 23 | | 94 | 6520 | 94 | 1648 | 92 | 434 | |
| 24 | | 96 | 6380 | 96 | 1656 | 95 | 439 | |
| 25 | 10820 | | | | | | | 0.9 |
| 26 | | 96 | 3431 | | | | | 1 |
| 27 | | 98 | 3334 | | | | | 0.4 |

(1) Cationic guar commercially available from Ashland Inc.
(2) Cationic guar commercially available from Rhodia

TABLE 5

Polymer Compositions and Shampoo Performance-Shampoos 5 and 6

| example | Cationic Substitution | Gal/Man ratio | Molecular weight | % T @ 600 nm aq polymer @1% | Visc/cps @ 1 wt % | % protein | % Nitrogen Total | % T @ 600 nm Shampoo 2 - [polymer] = 0.2 wt % |
|---|---|---|---|---|---|---|---|---|
| 1 | 0.196 | 0.643 | | 24 | 75400 | 1.31 | 1.59 | 62 |
| 2 | 0.189 | 0.665 | | 20 | 69200 | 1.31 | 1.54 | 72 |
| 3 | 0.203 | 0.587 | 329,000 | 40 | 38 | 1.19 | 1.67 | 86 |
| 5 | 0.198 | 0.557 | 441,000 | 39 | 72 | 1.38 | 1.63 | 89 |
| 5a | 0.267 | 0.54 | | 19 | | 1.06 | 2.16 | 97 |
| 8 | | | | 37 | 25 | | | 83 |
| 9 | 0.233 | 0.592 | | 41 | 50 | 1.13 | 1.87 | 90 |
| 10 | 0.25 | 0.568 | 953,000 | 45 | 1025 | 1.25 | 1.96 | 88 |
| 11 | 0.171 | 0.643 | 325,000 | 39 | 34 | 1.31 | 1.42 | 93 |
| 13 | | | | 43 | 24 | | | 91 |
| 15 | 0.196 | 0.566 | 580,000 | 51 | 360 | 1.38 | 1.64 | 88 |
| 16 (1) | 0.147 | 0.587 | 300,000 | 22 | 59 | 1.19 | 1.16 | 68 |
| 17 (1) | 0.171 | 0.574 | | 41 | 29 | 1.00 | 1.36 | 35 |
| 18 (1) | 0.158 | 0.605 | 1,140,000 | 46 | 4060 | 1.06 | 1.23 | 47 |
| 19 (1) | 0.225 | 0.576 | 1,070,000 | 40 | 3700 | 1.00 | 1.81 | 77 |
| 20 (2) | 0.231 | 0.632 | 837,000 | 86 | 960 | 0.25 | 1.7 | 97 |
| 21 (2) | 0.168 | 0.645 | 311,000 | 40 | 48 | 0.75 | 1.29 | 95 |
| 22 (2) | 0.14 | 0.624 | 1,030,000 | 36 | 5260 | 1.06 | 1.1 | 53 |
| 23 | 0.182 | 0.593 | 313,000 | 22 | 54 | 0.75 | 1.41 | 94 |
| 24 | 0.175 | 0.591 | 320,000 | 43 | 39 | 0.69 | 1.38 | 96 |
| 25 | 0.172 | 0.566 | 334,000 | 52 | 34 | 0.81 | 1.35 | |
| 26 | 0.171 | 0.567 | 334,000 | 52 | 40 | 1.00 | 1.38 | 96 |
| 27 | 0.168 | 0.651 | 255,000 | 55 | 18 | 0.69 | 1.33 | 98 |

| example | Shampoo 2 Visc/cps | % T @ 600 nm Shampoo 5 - [polymer] = 0.2 wt % | Shampoo 5 Visc/cps | ppm Silicone deposit on VB Hair from Shampoo 6 | Shampoo 6 Visc/cps | Polymer Wt % Insolubles |
|---|---|---|---|---|---|---|
| 1 | 6379 | | | | | |
| 2 | 6319 | | | | | |
| 3 | 4159 | | | | | |
| 5 | 4599 | | | | | |
| 5a | | | | | | |
| 8 | 7280 | 74 | 57 | 431 | 7860 | |
| 9 | 3539 | | | | | |
| 10 | 4849 | | | | | |
| 11 | 7360 | 93 | 46 | 770 | 8000 | |
| 13 | 3159 | | | | | |
| 15 | 7620 | 86 | 152 | 753 | | |
| 16 (1) | 5600 | 46 | 53 | 677 | | |
| 17 (1) | 10378 | | | | | |
| 18 (1) | 9280 | 40 | 890 | 941 | 29450 | |
| 19 (1) | 10200 | 72 | 880 | 1320 | 28700 | |
| 20 (2) | 8760 | 96 | 366 | 970 | 18020 | |
| 21 (2) | 6080 | 92 | 57 | 538 | 13780 | 0.3 |
| 22 (2) | 11600 | 13 | 588 | 653 | 31200 | |
| 23 | 6520 | 93 | 53 | 997 | 14800 | |
| 24 | 6380 | 92 | 53 | 756 | 14760 | |
| 25 | | | | | | 0.9 |

TABLE 5-continued

Polymer Compositions and Shampoo Performance-Shampoos 5 and 6

| | | |
|---|---|---|
| 26 | 3431 | 1 |
| 27 | 3334 | 0.4 |

(1) Cationic guar commercially available from Ashland Inc.
(2) Cationic guar commercially available from Rhodia *

TABLE 6

Shampoo Examples 28-35

| | | Pre-mix order | Example 28 Active Wt % | 29 Active Wt % | 30 Active Wt % | Comparative Examples 31 Active Wt % | 32 Active Wt % | 33 Active Wt % | 34 Active Wt % | 35 Active Wt % |
|---|---|---|---|---|---|---|---|---|---|---|
| Water | | 1 | | | | | | | | |
| SLES | Standapol ® ES2 | 2 | 12.0 | 8.0 | 12.0 | 12.0 | 8.0 | 10.0 | 12 | 8.0 |
| CAPB Cocamidopropyl Betaine | Amphasol ® CA | 3 | 2.0 | 2.0 | 2.0 | 2.0 | 2.0 | 2.0 | 2.0 | 2.0 |
| Sodium Chloride | | 8 | 1.0 | 1.0 | 1.0 | 1.0 | 1.0 | 1.0 | 1.0 | 1.0 |
| Cationic Guar | Polymer of Example 24 | 6 | 0.2 | 0.2 | 0.2 | | | | | |
| Carbomer | Aqualon 980 | 4 | | | 0.2 | | | | | |
| Dimethicanol emulsion | Dow Corning-1784 | 7 | | | 1.5 | | | | | |
| Phosphate Ester Oleth 5 Phosphate | Zenix ™ | | | 4 | | | 4 | 2 | | 4 |
| Cationic Guar | Comparative Polymer of Example 19 | 6 | | | | | | 0.2 | 0.2 | 0.2 |
| DMDM hydantoin | Glydant ® | 9 | 0.05 | 0.05 | 0.05 | | | | | |
| Methylchloroiso-thiazolinone | Kathon ® CG | 9 | | | | 0.05 | 0.05 | 0.05 | 0.05 | 0.05 |
| Sodium Hydroxide | | 5 | As needed | As needed | As needed | As needed | As needed | As needed | As needed | As needed |
| Viscosity at 30 rpm (cPs) | | | 1340 | 2300 | 5139 | 1,460 | 776 | 2,507 | 3,055 | 2,028 |
| % Transmittance @ 600 nm | | | 95 | 95.76 | 2 | 99.37 | 99.37 | 78.53 | 77 | 80.5 |
| Wet Comb Energy (g. force/mm) ± Std Dev V. Brown hair | | | 7884 ± 1168 | 4386 ± 355 | 4315 ± 721 | 7695+/− | 5309+/− | 3798+/− | 7951+/− | 4211+/− |
| Dry Comb Energy (g. force/mm) ± Std Dev V. Brown hair | | | 2662 ± 319 | 2037 ± 159 | 1934 ± 255 | 5508+/− | 2134+/− | 1516+/− | 2007+/− | 2047+/− |
| Wet Comb Energy (g. force/mm) ± Std Dev Bleached hair | | | 11695 ± 564 | 5928 ± 830 | 7464 ± 923 | 18260+/− | 15550+/− | 4909+/− | 9378+/− | 4224+/− |
| Dry Comb Energy (g. force/mm) ± Std Dev Bleached hair | | | 1400 ± 198 | 1421 ± 206 | 1411 ± 193 | 2260+/− | 2879+/− | 1377+/− | 1736+/− | 1831+/− |
| Coefficient of Friction ± Std Dev V. Brown hair | | | 0.1546 +/− 0.009 | 0.1463 +/− 0.006 | 0.1589 ± 0.005 | 0.1494 +/− 0.012 | 0.1403 +/− 0.007 | 0.1096 +/− 0.006 | 0.1088 +/− 0.008 | 0.1156 +/− 0.00902 |
| Coefficient of Friction ± Std Dev Bleached hair | | | 0.167 +/− 0.019 | 0.1420 +/− 0.0092 | 0.1595 ± 0.006 | 0.1558 +/− 0.0144 | 0.1405 +/− 0.009 | 0.1129 +/− 0.00283 | 0.128 +/− 0.0058 | 0.1355 +/− 0.0935 |
| Static Measurements $10^{-7}$ Coulombs V Brown | | | 3.98 | 0.1 | 2.69 | — | — | — | — | — |
| Static Measurements $10^{-7}$ Coulombs Bleached | | | 2.23 | 0.6 | 3.52 | — | — | — | — | — |

The wt % insoluble fraction of the polymers of the invention is shown to be >/=0.4 wt %, as shown in polymers of the invention in Examples 26 and 27. This amount of insoluble fraction is seen to be greater than the insoluble content of the comparative Example 21.

The results set forth in Tables 4, 5, and 6 demonstrate the surprising benefit of the polymers of the present invention in providing an increased level of clarity, as measured by % transmittance values greater than 85% at 600 nm wavelength, in the final shampoo formulation, with a diagnostic shampoo composition consisting of: 12% sodium lauryl ether sulfate (2EO)/2% cocamidopropyl betaine (CAPB)/1% NaCl and 0.2 wt % polymer, whereas the aqueous polymer solution has % transmittance values of <60% transmittance, when the polymer is present at a concentration of 1 wt %. The results in Tables 4 and 5 and 6 demonstrate the performance of the polymers of the invention across a broad range of molecular weights, cationic substitution levels, and nonionic substitution, and across a range of polymer structures, as defined by the ratio of galactose/mannose units in the polymer. The surprising benefits of the polymers of the invention are observed across broad ranges of cationic substitution, molecular weight, galactose/mannose ratios, and polymer protein content.

The results set forth in Table 5 also demonstrate the enhanced performance of the polymers of the invention as deposition agents for dispersed phase components, or benefit agents, such as silicone or zinc, onto substrates such as hair or skin.

The results set forth in Table 6 also demonstrate the enhanced performance of the polymers of the invention in combination with phosphate esters for delivering clear formulations with improved conditioning performance and antistatic performance.

It is not intended that the examples given here should be construed to limit the invention, but rather they are submitted to illustrate some of the specific embodiments of the invention. Various modifications and variations of the present invention can be made without departing from the scope of the appended claims.

We claim:

1. A polysaccharide composition, comprising:
   (a) a phosphate ester, and
   (b) a derivatized polysaccharide reaction product comprising the products of reaction of:
      a polygalactomannan comprising a water-insoluble fraction comprising greater than 10 wt % proteins and a reactive, water-soluble fraction,
      a cationic derivatizing agent,
      an oxidizing agent,
      a surfactant selected from the group consisting of an anionic surfactant, a nonionic surfactant, and combinations thereof, and
      a caustic aqueous solution,
   wherein the water-insoluble fraction is present in the polysaccharide composition at a range of from 0.4 to about 3 wt % of the polysaccharide composition; and
   wherein the derivatized polysaccharide reaction product provides:
   i) a clarity of less than 60% light transmittance at a wavelength of 600 nm for an aqueous solution comprising 1 wt % of the derivatized polysaccharide reaction product; and
   ii) a clarity of greater than 80% light transmittance at a wavelength of 600 nm for a surfactant system comprising 12 wt % sodium laureth sulfate, 2 wt % cocamidopropyl betaine, 1 wt % sodium chloride, and 0.2 wt % of the derivatized polysaccharide reaction product.

2. The composition of claim 1, wherein the polygalactomannan comprises guar.

3. The composition of claim 1, wherein the polygalactomannan has a weight average molecular weight of from about 5000 to about 10 million.

4. The composition of claim 1, wherein the phosphate ester is a phosphate ester of a $C_6$-$C_{32}$ fatty alcohol.

5. The composition of claim 4, wherein the phosphate ester is at least one of a monoester and a diester, wherein the monoester is represented by the structure of formula 1:

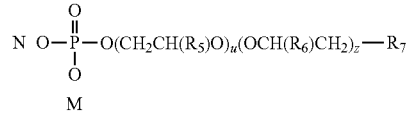

Formula 1 and wherein the diester is represented by the structure of formula 2:

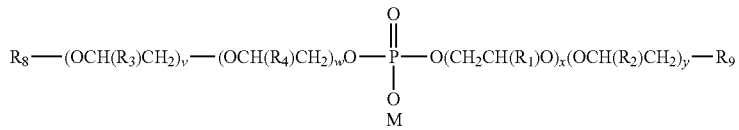

Formula 2 where:

M and N are hydrogen atoms or alkali metal atoms;

$R_1$, $R_2$, $R_3$, $R_4$, $R_5$, $R_6$ are hydrogen;

$R_7$, $R_8$ and $R_9$ are oleyl; and u, v, w, x, y, and z range from 0-20.

6. The composition of claim 5, wherein the phosphate ester is a mixture of mono- and di-esters and wherein u, v, x, z, w, and y are between 0 and 5.

7. The composition of claim 1, wherein the polygalactomannan is further reacted with at least one of a proteolytic enzyme and a hydrolytic enzyme to form the derivatized polysaccharide reaction product.

8. The composition of claim 1, wherein the oxidizing agent is selected from the group consisting of peroxides, peracids, persulfates, permanganates, perchlorates, hypochlorate, oxygen, and combinations thereof.

9. The composition of claim 8, wherein the oxidizing agent is a peroxide.

10. The composition of claim 1, wherein the polygalactomannan comprises guar splits.

11. The composition of claim 1, wherein the polygalactomannan is selected from the group consisting of guar, locust bean, cassia, fenugreek, honey locust, flame tree, and combinations thereof.

12. The composition of claim 1, wherein the phosphate ester is at least one of a monoester and a diester, wherein the monoester is represented by the structure of formula 1:

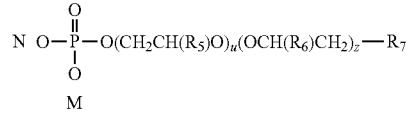

Formula 1 and wherein the diester is represented by the structure of formula 2:

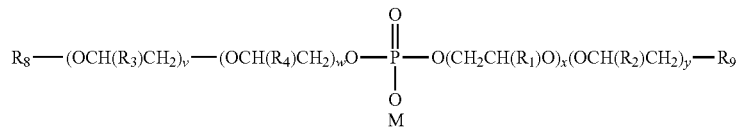

Formula 2 where:

M and N are hydrogen atoms or alkali metal atoms;
$R_1$, $R_2$, $R_3$, $R_4$, $R_5$, $R_6$ are hydrogen;
$R_7$, $R_8$ and $R_9$ are oleyl; and
u, v, w, x, y and z range from 0-20.

13. The composition of claim 12, wherein the phosphate ester is a mixture of mono- and di-esters wherein u, v, x, z, w, and y are between 0 and 5.

14. The composition of claim 1, wherein the surfactant is selected from the group consisting of polyoxyethylene (20) sorbitan monoleate, polyoxyethylene (20) sorbitan monolaurate, sodium laureth-13-carboxylate, lauric acid, oleic acid, and combinations thereof.

15. A personal care or a household care composition comprising the composition of claim 1.

16. A personal care or a household care composition comprising the composition of claim 1 in combination with a personal care or a household care active agent.

* * * * *